US008086552B2

(12) United States Patent
Randazzo et al.

(10) Patent No.: US 8,086,552 B2
(45) Date of Patent: Dec. 27, 2011

(54) DYNAMIC USER PROMPTING FOR PERTINENT CLINICAL INFORMATION

(75) Inventors: Michael Thomas Randazzo, South Jordan, UT (US); Randy Kent Secrist, West Jordan, UT (US); David John Steiner, Kaysville, UT (US)

(73) Assignee: General Electric Company, Schenectady, NY (US)

( * ) Notice: Subject to any disclaimer, the term of this patent is extended or adjusted under 35 U.S.C. 154(b) by 517 days.

(21) Appl. No.: 11/743,495

(22) Filed: May 2, 2007

(65) Prior Publication Data
US 2008/0275836 A1 Nov. 6, 2008

(51) Int. Cl.
*G06N 5/02* (2006.01)

(52) U.S. Cl. ............... 706/47; 706/46; 706/52; 706/62; 600/300; 600/301; 705/1.1; 705/2; 705/3

(58) Field of Classification Search ............... 706/8, 21, 706/45–47, 52, 59, 62, 924; 707/1, 3, 6; 705/2, 3; 600/300, 301
See application file for complete search history.

(56) References Cited

U.S. PATENT DOCUMENTS

| | | | | |
|---|---|---|---|---|
| 5,544,649 | A * | 8/1996 | David et al. .................... | 600/301 |
| 5,897,493 | A * | 4/1999 | Brown ........................... | 600/300 |
| 6,009,420 | A | 12/1999 | Fagg, III et al. | |
| 6,024,699 | A * | 2/2000 | Surwit et al. ................... | 600/300 |
| 6,049,794 | A | 4/2000 | Jacobs et al. | |
| 6,208,974 | B1 * | 3/2001 | Campbell et al. ................ | 705/3 |
| 6,272,481 | B1 | 8/2001 | Lawrence et al. | |
| 6,802,810 | B2 | 10/2004 | Ciarniello et al. | |
| 6,983,423 | B2 | 1/2006 | Dvorak et al. | |
| 7,230,529 | B2 | 6/2007 | Ketcherside, Jr. et al. | |
| 7,251,610 | B2 | 7/2007 | Alban et al. | |
| 7,256,708 | B2 * | 8/2007 | Rosenfeld et al. ....... | 340/870.01 |
| 7,315,825 | B2 * | 1/2008 | Rosenfeld et al. ................ | 705/2 |
| 7,475,019 | B2 * | 1/2009 | Rosenfeld et al. ................ | 705/2 |
| 2004/0059200 | A1 * | 3/2004 | Iliff .............................. | 600/300 |
| 2004/0260155 | A1 | 12/2004 | Ciarniello et al. | |
| 2006/0047538 | A1 * | 3/2006 | Condurso et al. ................ | 705/3 |
| 2006/0271408 | A1 * | 11/2006 | Rosenfeld et al. ................ | 705/3 |
| 2007/0094227 | A1 * | 4/2007 | Randazzo et al. .............. | 706/59 |
| 2007/0168223 | A1 | 7/2007 | Fors et al. | |

(Continued)

OTHER PUBLICATIONS

Aronsky et al., "Assessing the Quality of Clinical Data in a Computer-based Record for Calculating the Pneumonia Severity Index," Journal of the American Medical Informatics Association, vol. 7, No. 1, Jan./Feb. 2000, pp. 55-65. (11 pages).

(Continued)

*Primary Examiner* — Omar Fernandez Rivas
(74) *Attorney, Agent, or Firm* — Hanley, Flight & Zimmerman, LLC

(57) ABSTRACT

A method for dynamically prompting a caregiver for pertinent information about a patient uses a computer or processor operating as a rule-based system. The method includes receiving a first data input triggering a rule in a first rule queue requiring both a first data input and at least a second data input. The method further includes determining that the second data input is not available or is outdated, placing the rule in a second rule queue for later execution, and, when the second data input is available within a selected period of time, executing the rule, or otherwise, after the selected period of time, sending an electronic message to a caregiver to take action to provide the second data input.

20 Claims, 4 Drawing Sheets

U.S. PATENT DOCUMENTS

2008/0255880 A1* 10/2008 Beller et al. ............. 705/3
2008/0306759 A1* 12/2008 Ilkin et al. ............. 705/2

OTHER PUBLICATIONS

Bang et al., "Generation of Development Environments for the Arden Syntax," 1997 AMIA, Inc., pp. 313-317. (5 pages).

Brown et al., "Defining and predicting severe community-acquired pneumonia," Current Opinion in Infectious Diseases 2010, vol. 23, pp. 158-164. (7 pages).

Choi et al., "Adapting Current Arden Syntax Knowledge for an Object Oriented Event Monitor," AMIA 2003 Symposium Proceedings, p. 814. (1 page).

Downs et al., "Using Arden Syntax and Adaptive Turnaround Documents to Evaluate Clinical Guidelines," AMIA 2006 Symposium Proceedings, pp. 214-218. (5 pages).

Heckerling et al., "Clinical Prediction Rule for Pulmonary Infiltrates," Annals of Internal Medicine, 1990, vol. 113, pp. 664-670. (8 pages).

O'Brien, Sr, et al., "Clinical Indicators of Radiographic Findings in Patients With Suspected Community-Acquired Pneumonia: Who Needs a Chest X-Ray?," Journal of the American College of Radiology, vol. 3, No. 9, Sep. 2006, pp. 703-706. (4 pages).

Gennis et al., "Clinical Criteria for the Detection of Pneumonia in Adults: Guidelines for Ordering Chest Roentgenograms in the Emergency Department," The Journal of Emergency Medicine, vol. 7, 1989, pp. 263-268. (6 pages).

Jenders et al., "Medical Decision Support: Experience with Implementing the Arden Syntax at the Columbia-Presbyterian Medical Center," 1995 AMIA, Inc., pp. 169-173. (5 pages).

Lim et al., "Study of community acquired pneumonia aetiology (SCAPA) in adults admitted to hospital: implications for management guidelines," Thorax 2001, vol. 56, pp. 296-301. (6 pages).

Martinez et al., "Detection of Mycoplasma pneumoniae in adult community-acquired pneumonia by PCR and serology," Journal of Medical Microbiology 2008, vol. 57, pp. 1491-1495. (5 pages).

Metlay et al., "Testing Strategies in the Initial Management of Patients with Community-Acquired Pneumonia," Annals of Internal Medicine, vol. 138, No. 2, Jan. 21, 2003, pp. 109-119. (11 pages).

Miller, "Medical Diagnostic Decision Support Systems—Past, Present and Future: A Threaded Bibliography and Brief Commentary," Journal of the American Medical Informatics Association, vol. 1, No. 1, Jan/Feb 1994, pp. 8-27. (20 pages).

Miller et al., "Clinical Decision Support and Electronic Prescribing Systems: A Time for Responsible Thought and Action," Journal of the American Medical Informatics Association, vol. 12, No. 4, Jul/Aug 2005, pp. 403-409. (7 pages).

Miller et al., "The anatomy of decision support during inpatient care provider order entry (CPOE): Empirical observations from a decade of CPOE experience at Vanderbilt," Journal of Biomedical Informatics, Dec. 2005, vol. 38, No. 6, pp. 469-485. (30 pages).

* cited by examiner

DYNAMIC USER PROMPTING FOR PERTINENT CLINICAL INFORMATION

BACKGROUND OF THE INVENTION

This invention relates generally to clinical information systems, and more directly to clinical decision support systems.

In a clinical decision support system, a "rule" is intended to indicate what procedure or treatment to perform for a particular patient being monitored. For example, if a patient's measured potassium level dropped below 5, then a physician or nurse would be notified with this information. Thus, a rule would be written specifying that, when a patient's potassium level is below 5, send an email or a page to a particular nurse.

Rules written in decision support systems are typically written in a computer language such as JAVA®. Rules can depend upon more than one data input. If all of the data inputs are not available, the decision support system cannot process the rule accurately. This causes the decision support system to skip the rule or flag an error for an administrator to look at, at some later time. However, if all of the data inputs had been present, an alert might have been sent which might have notified clinicians of a potential problem.

For example, if a rule was set to watch both potassium and sodium levels in a patient and to signal an imbalance if the sodium level goes up and the potassium level goes down, there may be nothing to indicate an error if there are no measurements for sodium input to the decision support system. Also for example, if a new potassium level comes into the database and the sodium level measurement was from the previous day rather than within the last half hour as desired, the decision support system may not provide any decision or notify anyone immediately, as known decision support systems are configured to inform caregivers when certain events are happening. If a decision cannot be made, to prevent false notifications, no notifications are sent out, even though a problem may exist.

Although it may be possible to provide popup data windows on decision support systems, such windows are invasive and are unlikely to provide a suitable workflow for clinicians.

BRIEF DESCRIPTION OF THE INVENTION

Therefore, in one aspect, some configurations of the present invention provide a method for dynamically prompting a caregiver for pertinent information about a patient. The method uses a computer or processor operating as a rule-based system, and includes receiving a first data input triggering a rule in a first rule queue requiring both a first data input and at least a second data input. The method further includes determining that the second data input is not available or is outdated, placing the rule in a second rule queue for later execution, and, when the second data input is available within a selected period of time, executing the rule, or otherwise, after the selected period of time, sending an electronic message to a caregiver to take action to provide the second data input.

In another aspect, some configurations of the present invention provide an apparatus for dynamically prompting a user for pertinent clinical information. The apparatus includes a computer or processor, a rule processing engine having a first rule queue and a second rule queue. The second rule queue is associated with a timer configured to determine a wait time for rules in the second rule queue. The computer further includes and an electronic communication engine. The apparatus is configured to receive a first data input triggering execution of a rule in the first rule queue requiring both a first data input and at least a second data input, determine whether the second data input is not available or is outdated, and place the rule in the second rule queue for later execution when the second data input is not available or is outdated. The apparatus is further configured to, when the second data input is available within a selected period of time as determined by the timer, execute the rule. Otherwise, after the selected period of time, the apparatus is configured send an electronic message to a caregiver to take action to provide the second data input.

In still another aspect, some configurations of the present invention provide a machine readable medium or media having instructions recorded thereon that are configured to instruct a computer or processor to receive a first input triggering execution of a rule in a first rule queue requiring both a first data input and at least a second data input, determine whether the second data input is not available or is outdated, and place the rule in the second rule queue for later execution when the second data input is not available or is outdated. The instructions are also configured to instruct the computer or processor to, when the second data input is available within a selected period of time as determined by the timer, execute the rule, or otherwise, after the selected period of time, send an electronic message to a caregiver to take action to provide the second data input.

It will be appreciated that some configurations of the present invention can dynamically request missing information about a patient directly from an application from which a caregiver normally expects to receive alerts. Unlike known prior art methods, this request is or can be sent in a timely manner. Also, some configurations of the present invention advantageously allow the selection of which caregiver roles to prompt for the missing information.

DETAILED DESCRIPTION OF THE INVENTION

Figure 1:
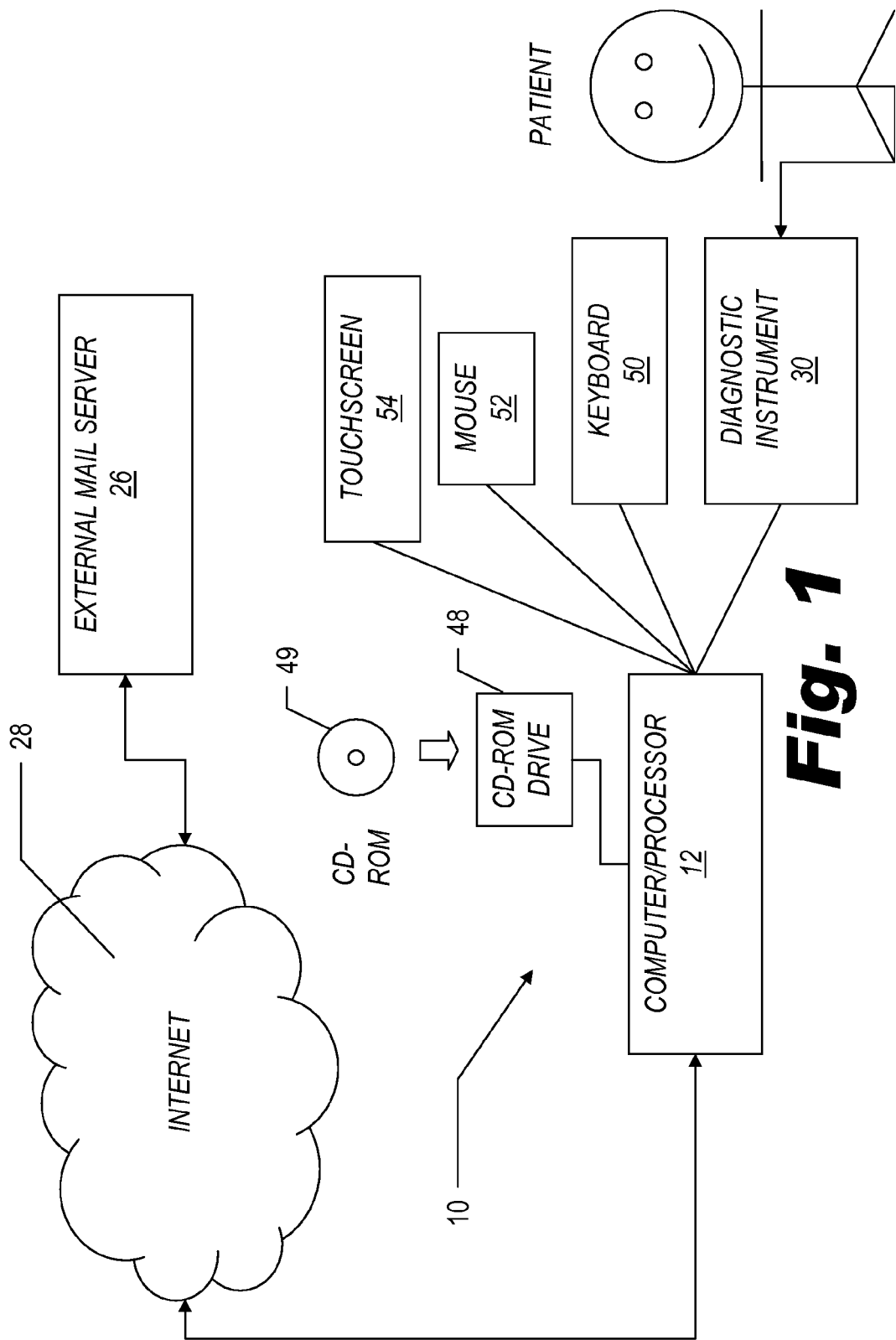
FIG. 1 is a block diagram of a system configuration utilizing an apparatus for dynamically prompting a user for pertinent clinical information.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Technical effects of the present invention include the timely alerting of specific caregivers for needed clinical information or tests to be run on a patient. In some configurations of the present invention and referring to FIGS. 1 and 2, these technical effects are achieved using an apparatus 10 for dynamically prompting a user for pertinent clinical information. The apparatus includes a computer or processor 12. Computer or processor 12 (hereinafter, "computer 12") can be a special purpose processor or a processor or computer programmed using software or firmware. Computer 12 includes (either as a special purpose processor, or by programming) a rule processing engine 14 having a first rule queue 16 and a second rule queue 18. Second rule queue 18 is associated with a timer 20 that is configured to determine a wait time for rules in second rule queue 18. Computer 12 also includes an electronic communication engine 22. Electronic communication engine 22 may include, for example, a mail handling program 24 in communication with an external mail server 26 over the Internet 28, and may also include data ports (such as USB ports, RS-232 ports, etc.) that communicate with diagnostic instruments 30 or other computers to receive clinical data. In some configurations, computer 12 is included in a diagnostic instrument 30. Electronic communication engine 22 may also include a database client 32 that communicates with an internal or external database server to receive clinical data.

Electronic communication engine 22 is also configured to receive a first data input 34 that triggers execution of a rule 36 in the first rule queue 16 requiring both a first data input 34 and at least a second data input 38. For example, consider a patient having a falling potassium level, which would normally be something that was clinically significant. However, the patient may have been prescribed a drug that has a falling potassium level as a side effect, making the falling potassium level important only if there is, at the same time, a rising sodium level, possibly indicating a condition needing treatment. On the other hand, in some configurations of the present invention, if the potassium level is falling, but sodium levels are unavailable or outdated, apparatus 10 can prompt a user to request sodium levels. Apparatus 10 can prompt for missing clinical variables, where one known variable individually is not interesting, but the known variable combined with one or more missing variables are of interest together, such as potassium levels and sodium levels, or potassium levels and heart rate.

Thus, in an exemplary case, first data input 34 is a data signal representing a blood potassium level. Rule 36 may be a rule specifying that a caregiver be alerted by an email message when the patient's potassium level drops below 6, but only if the patient's sodium level also rises above 50. The second data input 38 is the patient's sodium level.

In some configurations, apparatus 10 is configured to determine whether second data input 38 is not available or is outdated. For example, rule processing engine 14 checks whether second data input 38 has been received, and if so, whether a time stamp 40 associated with second data input 38 is within a specified time limit 42 (also referred to herein as "selected period of time 42"). If both criteria are met, the rule is executed normally; otherwise, the rule is placed in second rule queue 18 for later execution when second data input 38 is not presently available or is outdated. When second data input 38 is available within the selected period of time 42 as determined by timer 20, execute the rule; or otherwise, after the selected period of time 42, send an electronic message 44 to a caregiver 46 to take action to provide second data input 38.

In some configurations, apparatus 10 is further configured to apply selected period of time 42 to all rules for all patients. Selected period of time 42 may be input to apparatus 10 via any suitable method by a caregiver or other user and/or a default value may be provided by apparatus 10. However, in some configurations, apparatus 10 is further configured to apply a different selected period of time 42 to rules for different patients. In this case, along with rules, a caregiver or other user specifies the selected period of time 42 along with the set of rules for when the rules are entered for a patient. Any default period of time provided by apparatus 10 may still be applied unless overridden by a more specific selection. At the most specific level, some configurations of apparatus 10 are further configured to apply a different selected period of time for each rule for each patient. In this case, a caregiver or other user specifies a selected period of time 42 for each rule for each patient. Any default period of time provided by apparatus 10 may still be applied unless overridden by a rule for a particular patient and/or a specific rule for a specific patient.

Apparatus 10 may be programmed or otherwise configured to receive data specifying which data inputs (e.g., inputs 34 and 38, in the present example, potassium and sodium levels, respectively) are required for a rule to run and how or to whom to send an electronic message 44 to take action to provide the second data input. This data may be received as an addendum to a rule input by a caregiver via a keyboard 50, mouse 52, touch screen display 54, or any other suitable input device. In some configurations, an external mail server 26 may be specified in combination with a mail handling program 24 for sending and/or receiving electronic messages 44. In some configurations of the present invention, apparatus 10 is or can be further configured to receive an electronic message 44 (such as an email message) from a specified caregiver 46 to cancel a rule, and/or to receive an electronic message 44 from a specified caregiver 46 containing the second data input.

Figure 2:
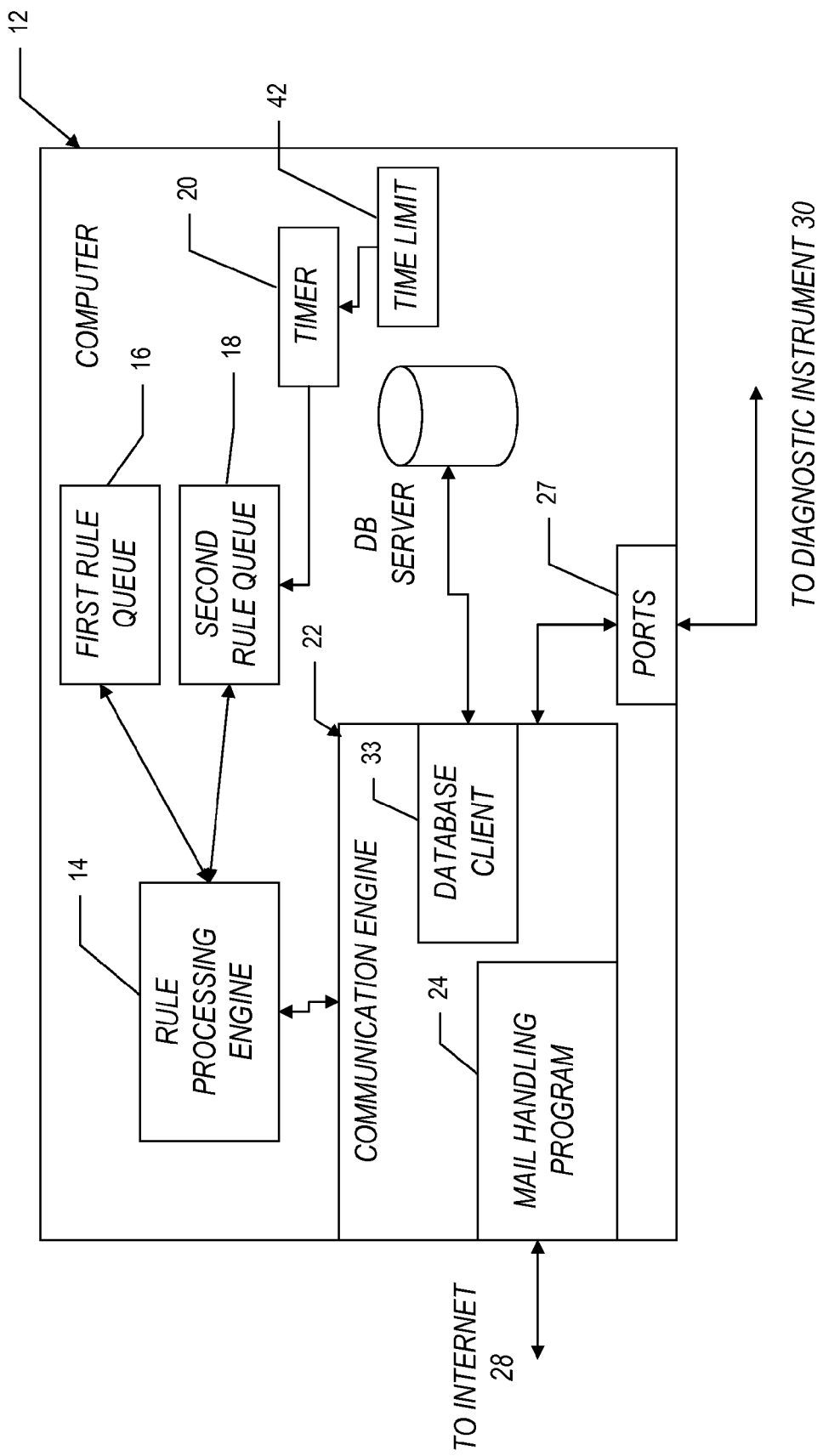
FIG. 2 is a functional block diagram of a configuration of apparatus for dynamically prompting a user for pertinent clinical information suitable for use in the system configuration of FIG. 1.

Also referring to FIGS. 1 and 2, apparatus 10 may be provided with a storage device or interface 48 capable of reading a machine readable medium or media 49 such as CD-ROM, CD-RW, DVD-R, DVD-RW, DVD+RW, flash memory, magnetic memory (such as a floppy diskette), a paper tape reader, etc. One or more of these media may have recorded on it machine readable instructions configured to instruct computer or processor 12 to perform configurations of the various methods described in more detail below. (The physical realization of computer programs may be divided arbitrarily. Thus, as used herein, the term "media" includes within its scope a collection of media, not all of which are required to be of a different type. Thus, a program divided across two CD-ROMs is considered to be recorded on "a machine readable medium or media," as would a program recorded partially on a floppy diskette and partially on a DVD-R.)

During the process of writing rules, some configurations of the present invention allow the rule writer to specify which data inputs are required for the rule to run and which individual caregiver role would typically fill out that information (e.g., "nurse," "physician," "specialist," etc). As data is input to the apparatus, if a rule is triggered by some, but not all of the required data, the rule is be flagged as partially run and moved to another queue. The apparatus waits for a period of time to see if the missing data arrives. As the queue of partially executed rules continues processing, if the information for a rule is not found after the configurable period of time, an alert is be sent to a caregiver who matches the role for the partially executed rule. The caregiver is thus able to chart the missing information and/or cancel the rule if the data is not available. The rule would, according, either reprocess or remove itself from the queue.

Figure 3:
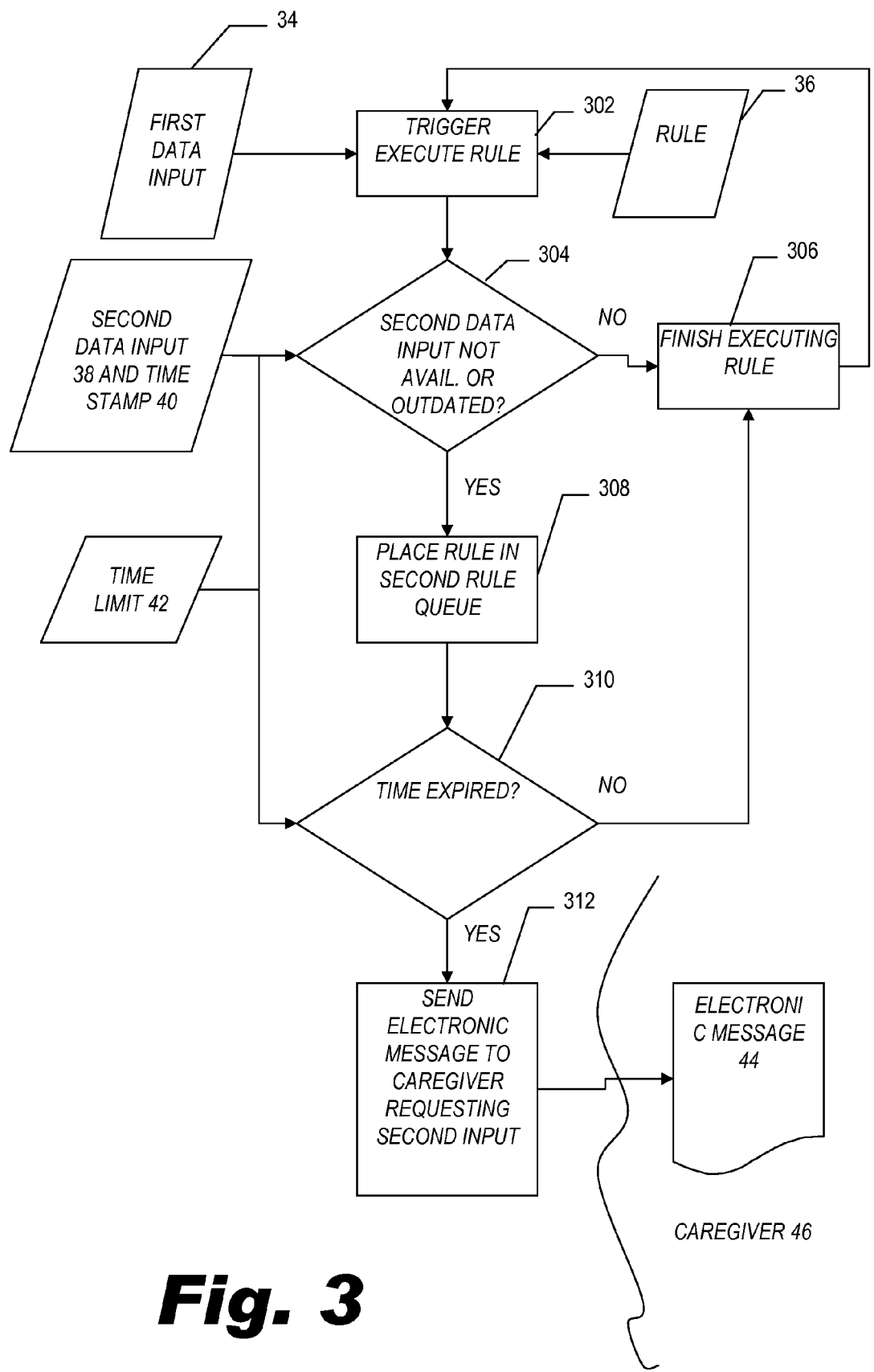
FIG. 3 is a data flow functional diagram of a configuration of the present invention, showing input of data and output of messages.
Figure 4:
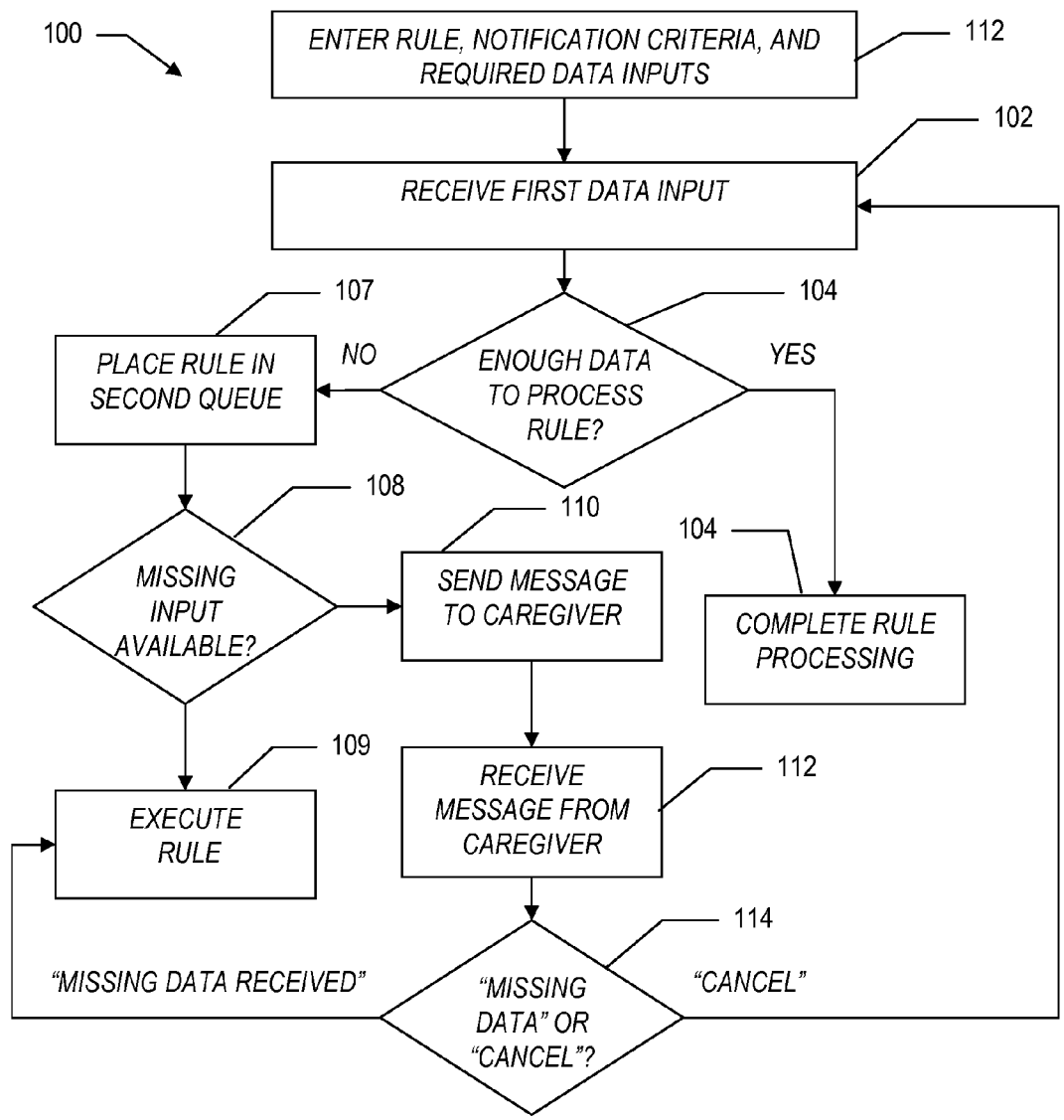
FIG. 4 is a flow chart of a method configuration of the present invention.

More particularly, referring to flowchart 100 of FIG. 3, after rules are entered, a computer or processor 12 operating as a rule-base system receives a first data input 34 at 102 that triggers a rule 36 in a first rule queue 16. First data input 34 may be manually entered by a user or received electronically by computer or processor 12.

The present invention does not prohibit or restrict computer or processor 12 from also operating on rules that require only a first data input 34, and/or rules that require more than two data inputs requiring both a first data input 34 and at least a second data input 38. Therefore, in many configurations of the present invention, a check is made at 104 to determine whether there is enough data to process rule 36, i.e., a whether a second data input required by the rule is not available or is outdated. (The phrase, "Whether a second data input required by the rule is not available or is outdated," should be read as including within its scope configurations in which either of the conditions is checked as well as configurations in which both conditions are or can be checked.) If a second data input is available (and, in some configurations, not outdated), the rule completes processing in rule processing engine 14 at 106. Otherwise, rule 36 is placed in a second rule queue 18 for later execution. When second data input 38 is available within a selected period of time 42, the rule is executed (i.e., processed) by rule processing engine 14, otherwise, after the selected period of time 42, an electronic message 44 is sent to a caregiver 46 to take action to provide second data input 38.

Method configurations of the present invention can be performed on the same computer or processor 12 for a plurality of patients, and the selected period of time 42 can be the same for all of the patients, or the selected period of time 42 can be selected separately for each of the patients in some configurations. Some configurations of the method include selecting a period of time 42 separately for each rule. ("Selecting a period of time 42 separately for each patient" or "for each rule" is intended to include within its scope configurations in which a period of time 42 can be selected by default for a patient and/or a rule.)

In some configurations, the method further includes receiving data specifying which inputs are required a rule to run at 108 and how or to whom to send an electronic message to take action to provide second data input 38. The receiving of data specifying which inputs are required and how or to whom to send a message may be provided when rules are input to apparatus 10. Also some configurations of the present invention further include receiving an electronic message 44 at 110 from caregiver 46 to cancel the rule, and/or receiving an electronic message 44 from caregiver 46 containing second data input 38 at 112. In configurations in which both a rule cancellation or a second data input can be received, a decision at 114 may be made as to which type of electronic message 44 has been received at 116. The decision at 114 may be made, for example, by electronic communication engine 22, mail handling program 24, and/or rule processing engine 14 interpreting the syntax and format of electronic message 44.

Thus, it will be observed that some configurations of the present invention can dynamically request missing information about a patient directly from an application from which a caregiver normally expects to receive alerts. Unlike known prior art methods, this request is or can be sent in a timely manner. Also, some configurations of the present invention advantageously allow the selection of which caregiver roles to prompt for the missing information.

While the invention has been described in terms of various specific embodiments, those skilled in the art will recognize that the invention can be practiced with modification within the spirit and scope of the claims.

What is claimed is:

1. A method for dynamically prompting a caregiver for pertinent information about a patient, said method using a computer or processor operating as a rule-based system, each rule indicating a particular action to be taken for the patient based on a monitored condition, said method comprising:
   receiving a first data input triggering a first rule in a first rule queue requiring both a first data input and at least a second data input;
   determining that the second data input is not available or is outdated;
   placing the first rule in a second rule queue for later execution while awaiting the second data input; and
   when the second data input is available within a selected period of time, executing the first rule; or otherwise, after the selected period of time, sending an electronic message to a caregiver to take action to provide the second data input.

2. A method in accordance with claim 1 wherein the method is performed on the same computer or processor for a plurality of patients, and the selected period of time is the same for all of said patients.

3. A method in accordance with claim 1 wherein the method is performed on the same computer or processor for a plurality of patients, and the selected period of time is selected separately for each said patient.

4. A method in accordance with claim 1 wherein the method is performed on the same computer or processor for a plurality of patients, and the selected period of time is selected separately for each said rule.

5. A method in accordance with claim 1 further comprising receiving data specifying which inputs are required for the first rule to execute and how or to whom to send an electronic message to take action to provide the second data input.

6. A method in accordance with claim 1 further comprising receiving an electronic message from the caregiver to cancel the first rule.

7. A method in accordance with claim 1 further comprising receiving an electronic message from the caregiver containing the second data input.

8. An apparatus for dynamically prompting a user for pertinent clinical information, said apparatus comprising a computer or processor, a rule processing engine having a first rule queue and a second rule queue, the second rule queue associated with a timer configured to determine a wait time for rules in the second rule queue, and an electronic communication engine, each rule indicating a particular action to be taken for the patient based on a monitored condition, said apparatus configured to:
   receive a first data input triggering execution of a first rule in the first rule queue requiring both a first data input and at least a second data input;
   determine whether the second data input is not available or is outdated;
   place the first rule in the second rule queue for later execution while awaiting the second data input when the second data input is not available or is outdated; and when the second data input is available within a selected period of time as determined by the timer, execute the first rule; or otherwise, after the selected period of time, send an electronic message to a caregiver to take action to provide the second data input.

9. An apparatus in accordance with claim 8 wherein the apparatus is configured to apply the selected period of time to all rules for all patients.

10. An apparatus in accordance with claim 8 wherein the apparatus is configured to apply a different selected period of time to rules for different patients.

11. An apparatus in accordance with claim 8 wherein the apparatus is configured to apply a different selected period of time for each rule for each patient.

12. An apparatus in accordance with claim 8 further configured to receive data specifying which inputs are required for the first rule to execute and how or to whom to send an electronic message to take action to provide the second data input.

13. An apparatus in accordance with claim 8 further configured to receive an electronic message from the caregiver to cancel the first rule.

14. An apparatus in accordance with claim 8 further configured to receive an electronic message from the caregiver containing the second data input.

15. A machine readable medium or media having instructions recorded thereon that are configured to instruct a computer or processor to:
   receive a first input triggering execution of a first rule in a first rule queue requiring both a first data input and at least a second data input, the first rule indicating a particular action to be taken for the patient based on a monitored condition;
   determine whether the second data input is not available or is outdated;
   place the first rule in the second rule queue for later execution while awaiting the second data input when the second data input is not available or is outdated; and
   when the second data input is available within a selected period of time as determined by a timer, execute the first rule; or otherwise, after the selected period of time, send an electronic message to a caregiver to take action to provide the second data input.

16. A medium or media in accordance with claim 15 wherein said instructions include instructions that are configured to instruct the computer or processor to apply the selected period of time to all rules for all patients, each rule indicating a particular action to be taken for the patient based on a monitored condition.

17. A medium or media in accordance with claim 15 wherein said instructions include instructions that are configured to instruct the computer or processor to apply a different selected period of time to rules for different patients.

18. A medium or media in accordance with claim 15 wherein said instructions include instructions that are configured to instruct the computer or processor to apply a different selected period of time for each rule for each patient.

19. A medium or media in accordance with claim 15 wherein said instructions further configured to instruct the computer or processor to receive data specifying which inputs are required for the first rule to execute and how or to whom to send an electronic message to take action to provide the second data input.

20. A medium or media in accordance with claim 15 wherein said instructions further configured to instruct the computer or processor to receive an electronic message from the caregiver to cancel the first rule, to receive an electronic message from the caregiver containing the second data input, or both.

* * * * *